(12) United States Patent
Hasegawa

(10) Patent No.: US 11,123,265 B2
(45) Date of Patent: Sep. 21, 2021

(54) MEDICATION SUPPORT APPARATUS, MEDICATION SUPPORT SYSTEM, MEDICATION SUPPORT METHOD, AND PROGRAM

(71) Applicant: FUJIFILM Corporation, Tokyo (JP)

(72) Inventor: Kazuhide Hasegawa, Ashigarakami-gun (JP)

(73) Assignee: FUJIFILM Corporation, Tokyo (JP)

( * ) Notice: Subject to any disclaimer, the term of this patent is extended or adjusted under 35 U.S.C. 154(b) by 114 days.

(21) Appl. No.: 16/506,449

(22) Filed: Jul. 9, 2019

(65) Prior Publication Data

US 2019/0328618 A1 Oct. 31, 2019

Related U.S. Application Data

(63) Continuation of application No. PCT/JP2018/004661, filed on Feb. 9, 2018.

(30) Foreign Application Priority Data

Feb. 28, 2017 (JP) .............................. JP2017-036753

(51) Int. Cl.
*A61J 7/00* (2006.01)
*G07F 17/00* (2006.01)
*G16H 20/10* (2018.01)

(52) U.S. Cl.
CPC ........ *A61J 7/0076* (2013.01); *G07F 17/0092* (2013.01); *G16H 20/10* (2018.01); *A61J 2200/30* (2013.01)

(58) Field of Classification Search
CPC .... A61J 7/0076; A61J 2200/30; G16H 20/10; G07F 17/0092
See application file for complete search history.

(56) References Cited

U.S. PATENT DOCUMENTS 8,797,167 B2 * 8/2014 Bangera ................. G16H 40/67
340/573.1
9,035,777 B2 * 5/2015 Bangera ................. G16H 20/10
340/573.1
(Continued)

FOREIGN PATENT DOCUMENTS

JP 2014-36731 A 2/2014
JP 2015-228082 A 12/2015
(Continued)

OTHER PUBLICATIONS

Extended European Search Report, dated Jan. 23, 2020, for European Application No. 18760652.0.
(Continued)

*Primary Examiner* — Michael Collins
(74) *Attorney, Agent, or Firm* — Birch, Stewart, Kolasch & Birch, LLP

(57) ABSTRACT

There are provided a medication support apparatus, a medication support system, a medication support method, and a program capable of reliably checking that a correct user has taken a correct medicine. A medication support apparatus includes: a medication instruction information acquisition unit 12 that acquires medication instruction information including medicine information and user information; a medicine package holding unit 16 that holds a medicine package; a user checking unit 14 that checks whether or not a user corresponds to the user information; a medicine package providing unit 18 that takes out the medicine package corresponding to the checked user from the medicine package holding unit 16; a medicine package checking unit 20 that checks whether or not the medicine package or the medicine in the medicine package corresponds to the medicine information; an action recognition unit 22 that recognizes an action of the user; and a medication determination unit 24 that determines whether or not medication has (Continued)

been performed, according to the medication instruction information based on the medication instruction information, a checking result of the user checking unit 14, a checking result of the medicine package checking unit 20, and a recognition result of the action recognition unit 22.

12 Claims, 15 Drawing Sheets

(56) References Cited

U.S. PATENT DOCUMENTS

| | | | |
|---|---|---|---|
| 9,081,885 B2* | 7/2015 | Bangera | A61J 7/0481 |
| 9,387,156 B2* | 7/2016 | Bangera | G06Q 10/0639 |
| 9,390,234 B2* | 7/2016 | Bangera | G16H 20/13 |
| 9,424,396 B2* | 8/2016 | Bangera | A61B 5/0077 |
| 2002/0032582 A1* | 3/2002 | Feeney, Jr. | G16H 20/13 |
| | | | 705/2 |
| 2002/0169637 A1* | 11/2002 | Akers | G16H 40/67 |
| | | | 705/3 |
| 2011/0275051 A1 | 11/2011 | Hanina et al. | |
| 2014/0002631 A1 | 1/2014 | Amano et al. | |
| 2014/0039445 A1* | 2/2014 | Austin | A61J 7/0084 |
| | | | 604/404 |
| 2014/0195042 A1* | 7/2014 | Adler | G16H 20/13 |
| | | | 700/233 |
| 2015/0272825 A1 | 10/2015 | Lim et al. | |
| 2015/0317453 A1* | 11/2015 | Cunningham | B65D 83/0409 |
| | | | 700/232 |

FOREIGN PATENT DOCUMENTS

| | | |
|---|---|---|
| JP | 2016-67840 A | 5/2016 |
| JP | 2016-85461 A | 5/2016 |
| JP | 2016-182185 A | 10/2016 |
| WO | WO 2015/196293 A1 | 12/2015 |

OTHER PUBLICATIONS

Hitachi, "Medication Support Cloud Service," Hitachi Social Innovation Forum Oct. 27, 2016, 2 pages.
Japanese Office Action, dated Sep. 29, 2020, for corresponding Japanese Application No. 2019-502849, with an English translation.
Hitachi Social Innovation Forum 2016, Oct. 27, 2016, 2 pages.
International Preliminary Report on Patentability and Written Opinion of the International Searching Authority (Forms PCT/IB/326, PCT/IB/373 and PCT/ISA/237) for International Application No. PCT/JP2018/004661, dated Sep. 12, 2019, with Engiish translation.
International Search Report (Form PCT/ISA/210) for International Application No. PCT/JP2018/004661, dated May 1, 2018.

\* cited by examiner

FIG. 10

```
              FUJI TARO
DATE 10, AFTER BREAKFAST No.1234
DATE 10, AFTER LUNCH      No.1235
DATE 10, AFTER DINNER     No.1236
DATE 11, AFTER BREAKFAST No.1244
DATE 11, AFTER LUNCH      No.1245
DATE 11, AFTER DINNER     No.1246
```

MEDICATION SUPPORT APPARATUS, MEDICATION SUPPORT SYSTEM, MEDICATION SUPPORT METHOD, AND PROGRAM

CROSS-REFERENCE TO RELATED APPLICATIONS

The present application is a Continuation of PCT International Application No. PCT/JP2018/004661 filed on Feb. 9, 2018 claiming priority under 35 U.S.C § 119(a) to Japanese Patent Application No. 2017-036753 filed on Feb. 28, 2017. Each of the above applications is hereby expressly incorporated by reference, in their entirety, into the present application.

BACKGROUND OF THE INVENTION

1. Field of the Invention

The present invention relates to a medication support apparatus, a medication support system, a medication support method, and a program.

2. Description of the Related Art

Conventionally, various apparatuses for supporting medication have been proposed or provided.

A medication support apparatus described in JP2016-067840A notifies that this is a medication time by voice guidance and screen display in a case where a medication time set in advance comes, and delivers a medicine case from a cassette to a discharge port in a case where the user takes out the medicine case.

SUMMARY OF THE INVENTION

However, it has been difficult in practice to reliably check that a correct user has taken a correct medicine.

The medication support apparatus described in JP2016-067840A notifies that this is a medication time by voice guidance and screen display in a case where the medication time set, in advance comes, and delivers a medicine case from the cassette to the discharge port, in a case where the user takes out the medicine case. However, in a case where there are a plurality of users are, it is not possible to check whether the medicine case has passed to the correct user or the medicine case has passed to others. In addition, whether or not the medicine passed to the user is a prescribed drug depends on whether or not both storage of the medicine in the medicine case and storage of the medicine case in the cassette have been correctly performed. Therefore, there is concern about the reliability. In addition, it is up to the user's action whether or not the medicine in the medicine case passed to the user is taken, and checking is not performed.

It is an object of the present invention to provide a medication support apparatus, a medication support system, a medication support method, and a program capable of reliably checking that a correct user has taken a correct medicine.

In order to achieve the aforementioned object, a medication support apparatus according to a first aspect of the present invention comprises: a medication instruction information acquisition unit that acquires medication instruction information including medicine information indicating a packaged medicine and user information indicating a user who takes the medicine; a medicine package holding unit that holds a medicine package in which the medicine is packaged; a user checking unit that checks whether or not a user corresponds to the user information; a medicine package providing unit that takes out the medicine package corresponding to the checked user from the medicine package holding unit; a medicine package checking unit that checks whether or not the medicine package or the medicine in the medicine package corresponds to the medicine information; an action recognition unit that recognizes an action of the user; and a medication determination unit that determines whether or not medication has been performed according to the medication instruction information based on the medication instruction information, a checking result of the user checking unit, a checking result of the medicine package checking unit, and a recognition result of the action recognition unit.

According to this aspect, the medication instruction information including the medicine information indicating the packaged medicine and the user information indicating the user who takes the medicine is acquired. It is checked whether or not the user corresponds to the user information in the medication instruction information. The medicine package corresponding to the checked user is taken out, and it is checked whether or not the medicine package or the medicine in the medicine package corresponds to the medicine information in the medication instruction information. The user's action is recognized, and it is determined whether or not medication has been performed according to the medication instruction information based on the medication instruction information, the user checking result, the checking result of the medicine package or the medicine, and the user action recognition result. Therefore, it is reliably checked that the correct user has taken the correct medicine.

A medication support apparatus according to a second aspect of the present invention comprises a recording unit that records the medication instruction information and medication result information including a determination result of the medication determination unit, for each user, so as to be associated with each other.

A medication support apparatus according to a third aspect of the present invention comprises an output unit that outputs the medication instruction information and medication result information including a determination result of the medication determination unit, for each user, so as to be associated with each other.

A medication support apparatus according to a fourth aspect of the present invention further comprises a physical condition information acquisition unit that acquires physical condition information indicating a physical condition of the user, and the output unit outputs the physical condition information acquired by the physical condition information acquisition unit.

In a medication support apparatus according to a fifth aspect of the present invention, the medication instruction information acquisition unit acquires at least a part of the medication instruction information by reading a code or a character attached to the medicine package.

In a medication support apparatus according to a sixth aspect of the present invention, the action recognition unit recognizes the action of the user through an image obtained by imaging the user or interaction with the user.

In a medication support apparatus according to a seventh aspect of the present invention, the medication instruction information includes medication time information indicating a time to take the medicine, the action recognition unit recognizes at least a medication time of the user, and the medication determination unit determines whether or not medication has been performed according to the medication time information based on the medication time information and a recognition result of the medication time.

In a medication support apparatus according to an eighth aspect of the present invention, the medication instruction information includes the medication time information associated with a meal time of the user, the action recognition unit recognizes an eating action and a medication action of the user, and the medication determination unit determines whether or not medication has been performed according to the medication time information based on the medication time information and a recognition result of the eating action and the medication action. According to this aspect, since it is possible to determine an appropriate medication timing by acquiring the medication time information and recognizing the user's eating action, it is possible to reliably check that the user has taken the medicine at an appropriate time, such as after a meal, before a meal, and between meals.

In a medication support apparatus according to a ninth aspect of the present invention, the medicine package checking unit recognizes the medicine package or the medicine in the medicine package by reading a code or a character attached to the medicine package.

In a medication support apparatus according to a tenth aspect of the present invention, the medicine package checking unit recognizes the medicine package or the medicine in the medicine package by performing image recognition on an image obtained by imaging the medicine package.

A medication support apparatus according to an eleventh aspect of the present invention further comprises a communication unit that makes an inquiry to the user.

A medication support system according to a twelfth aspect of the present invention comprises the medication support apparatus and at least one of a packaging apparatus for packaging the medicine or an audit support apparatus for supporting an audit of the medicine.

In a medication support system according to a thirteenth aspect of the present invention, the medication instruction information acquisition unit acquires the medication instruction information from at least one of the packaging apparatus or the audit support apparatus. According to this aspect, since information acquired at the time of packaging by the packaging apparatus or audit by the audit support apparatus can be reused as medication instruction information, it is possible to increase the reliability of the checking result.

A medication support method according to a fourteenth aspect of the present invention comprises: a step of acquiring medication instruction information including medicine information indicating a packaged medicine and user information indicating a user who takes the medicine; a user checking step of checking whether or not a user corresponds to the user information; a step of taking out a medicine package corresponding to the checked user from a medicine package holding unit that holds the medicine package in which the medicine is packaged; a medicine package checking step of checking whether or not the medicine package or the medicine in the medicine package corresponds to the medicine information; an action recognition step of recognizing an action of the user; and a step of determining whether or not medication has been performed according to the medication instruction information based on the medication instruction information, a checking result of the user checking step, a checking result of the medicine package checking step, and a recognition result of the action recognition step.

Aerogram according to a fifteenth aspect of the present invention causes a computer to execute: a step of acquiring medication instruction information including medicine information indicating a packaged medicine and user information indicating a user who takes the medicine; a user checking step of checking whether or not a user corresponds to the user information; a step of taking out a medicine package corresponding to the checked user from a medicine package holding unit that holds the medicine package in which the medicine is packaged; a medicine package checking step of checking, whether or not the medicine package or the medicine in the medicine package corresponds to the medicine information; an action recognition step of recognizing an action of the user; and a step of determining whether or not medication has been performed according to the medication instruction information based on the medication instruction information, a checking result of the user checking step, a checking result of the medicine package checking step, and a recognition result of the action recognition step.

According to the present invention, it is possible to reliably check that a correct user has taken a correct medicine.

BRIEF DESCRIPTION OF THE DRAWINGS

FIG. 10 is an explanatory diagram of an example of medicine package management, information.

DESCRIPTION OF THE PREFERRED EMBODIMENTS

Hereinafter, forms for implementing a medication, support apparatus, a medication support system, a medication support method, and a program according to the present invention will be described with reference to the accompanying diagrams.

Figure 1:
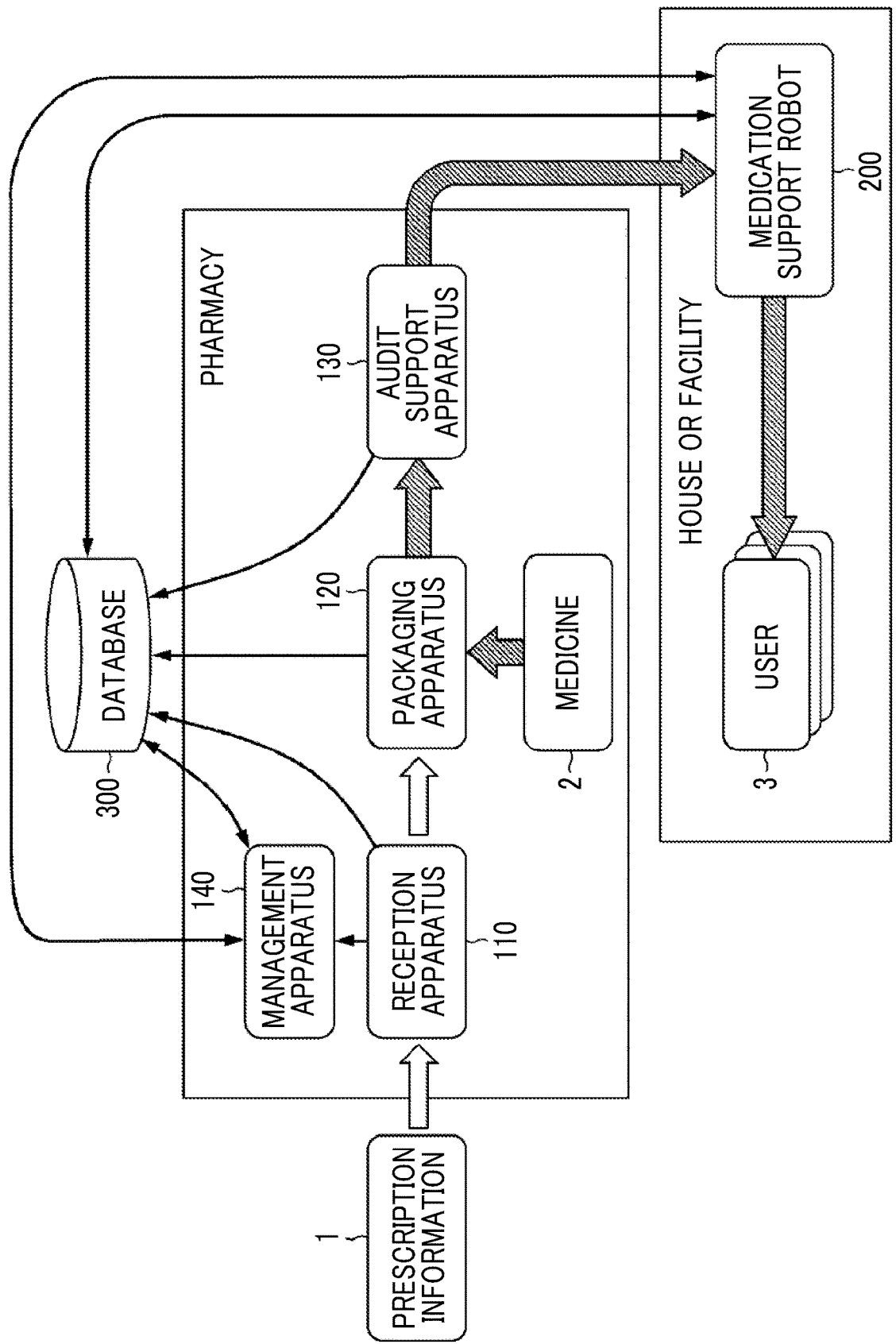
FIG. 1 is a system configuration diagram showing a medication support system including a medication support robot that is an example of a medication support apparatus according to the present invention.

FIG. 1 is a system configuration diagram, showing a medication support system including a medication support robot that is an example of the medication support apparatus according to the present invention.

The medication support system in this example is configured to include: a reception apparatus 110 for receiving prescription information 1; a packaging apparatus 120 for packaging a medicine 2 corresponding to the prescription information 1; an audit support apparatus 130 for supporting the audit of the packaged medicine 2; a management apparatus 140 for performing various kinds of management processing; a medication support robot 200 (one form of the medication support apparatus) for supporting the taking of the medicine 2 (hereinafter, referred to as "medication") of a user 3; and a database 300 for storing various kinds of information obtained by the reception apparatus 110, the packaging apparatus 120, the audit support apparatus 130, the management apparatus 140, and the medication support robot 200.

In this example, the reception apparatus 110, the packaging apparatus 120, the audit support apparatus 130, and the management apparatus 140 are provided in the prescription pharmacy, and the medication support robot 200 is provided in the house of the user 3 or a facility used by the user 3. However, places where these apparatuses are provided are not particularly limited.

The reception apparatus 110 can acquire the prescription information 1 for the user, for example, by optically reading a prescription. The prescription information 1 input by a doctor at a terminal or the like in a hospital may be acquired by communication. The prescription information 1 includes user information and prescription content for the user. The prescription information 1 includes, for example, the name of the user, the age or date of birth of the user, the name of the medicine, dosage, medication time, and information indicating a hospital or a doctor. The reception apparatus 110 in, this example transmits the prescription information 1 to the management apparatus 140, and stores the prescription information 1 in the database 300.

The packaging apparatus 120 packages, for example, the medicine 2 picked up by a pharmacist in a packaging material. Hereinafter, the packaging material and the medicine 2 packaged in the packaging material are referred to as a "medicine package". The packaging apparatus 120 in this example stores packaging form information indicating the form of packaging in the database 300. The packaging apparatus 120 may image the medicine 2 (or the medicine package) at the time of packaging and store an image obtained by the imaging in the database 300. In addition, the packaging apparatus 120 may assign identification information (medicine package identifier (ID)) of a medicine package 52 to each medicine package 52 at the time of packaging and stores the information in the database 300.

"Packaging" refers to packaging (dividing) the prescribed medicine every single dose. Depending on the prescription content, there are a case where a plurality of medicines of different types are packaged in one packaging material, a case where a plurality of medicines of the same type are packaged in one packaging material, and a case where only one medicine is packaged in one packaging material. Examples of the form of the medicine to be packaged include tablets and capsules, but are not particularly limited. Examples of the packaging material include paper and plastic, but are not particularly limited.

Figure 2:
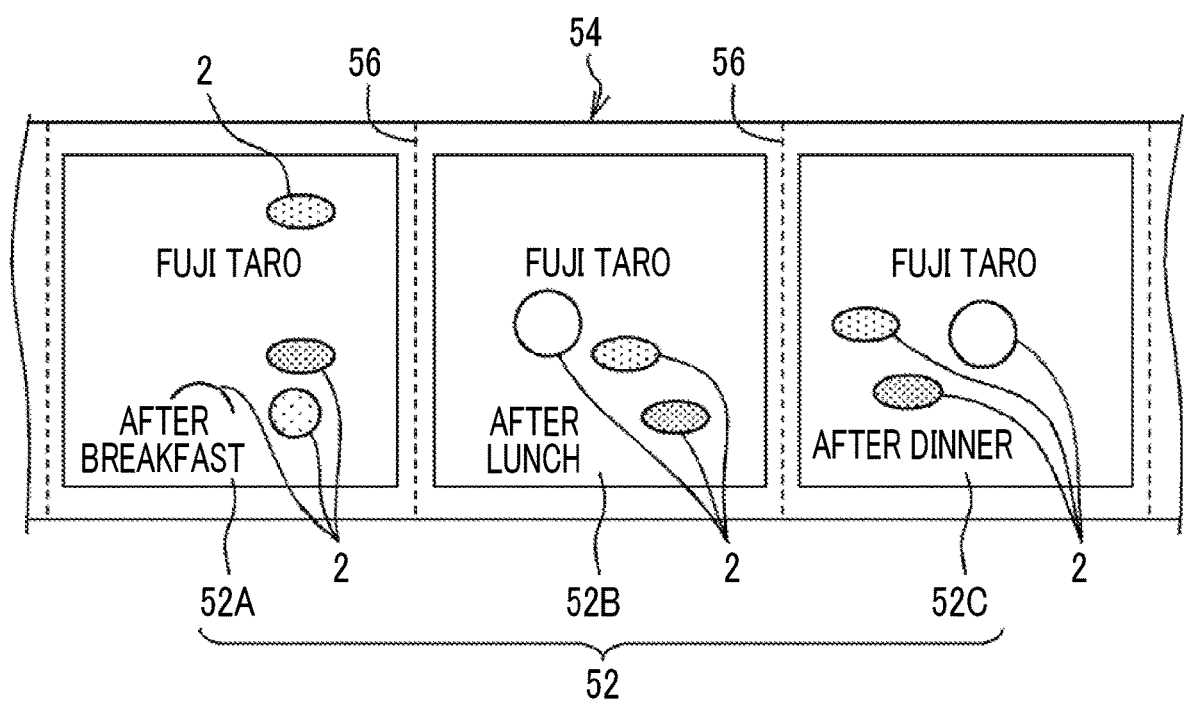
FIG. 2 is an explanatory diagram showing an example of packaging.

FIG. 2 shows an example of simple packaging. In FIG. 2, a strip-shaped medicine package bandage 54 includes a medicine package 52A (medicine package for morning) in which four kinds of medicines 2 to be taken after breakfast are packaged, a medicine package 52B (medicine package for lunch) in which three kinds of medicines 2 to be taken after lunch are packaged, and a medicine package 52C (medicine package for evening) in which three kinds of medicines 2 to be taken after evening are packaged. In this example, perforations 56 for cutting (cutting line) are formed between the plurality of medicine packages 52 (52A, 52B, and 52C). In this example, the user's name and medication time ("after breakfast", "after lunch", and "after dinner") are printed on each of the plurality of medicine packages 52 (52A, 52B, and 52C). However, printing is not essential. Other examples of packaging will be described later.

The audit support apparatus 130 checks whether or not the medicine 2 packaged by the packaging apparatus 120 is the same as the prescription information 1. The audit support apparatus 130 in this example has an audit function of imaging the medicine package 52 packaged by the packaging apparatus 120 to image-recognize the medicine 2 in the medicine package 52 and checking whether or not the medicine 2 in the medicine package 52 matches the medicine indicated by the prescription information 1. In addition, the audit support apparatus 130 in this example has a function of storing an image obtained by imaging the medicine package 52 (hereinafter, referred to as a "medicine package image") in the database 300 and a function of extracting an image of a region of the medicine 2 (hereinafter, referred to as a "medicine image") from the medicine package image and storing the extracted medicine image in the database 300. In addition, the audit support apparatus 130 in this example has a function of generating medication instruction information and storing the medication instruction information in the database 300.

The management apparatus 140 is configured by, for example, a computer apparatus.

Figure 3:
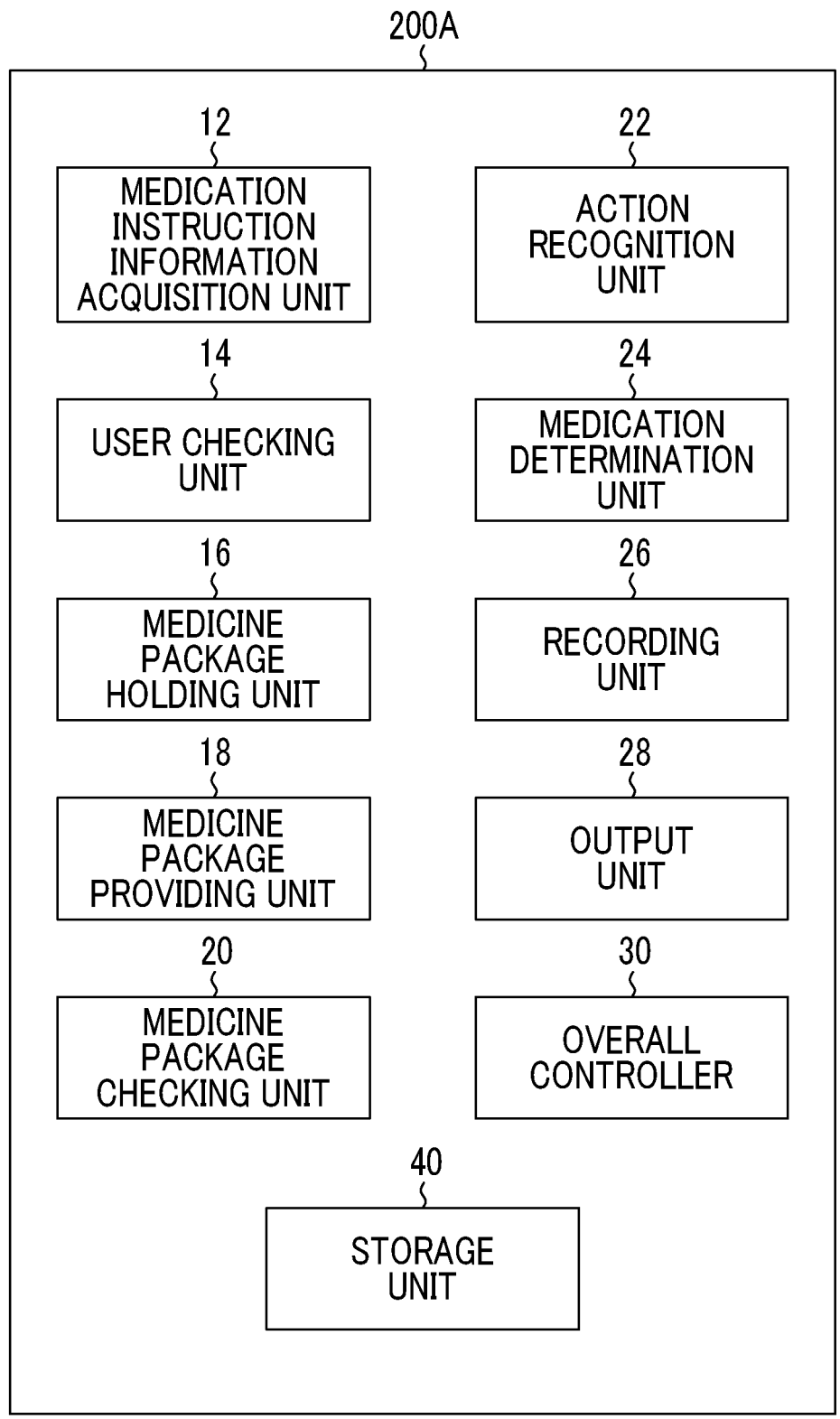
FIG. 3 is a block diagram showing an example of the internal configuration of a medication support robot in a first embodiment.

FIG. 3 is a block diagram showing an example of the internal configuration in a first embodiment of the medication support robot 200 shown in FIG. 1.

A medication support robot 200A in this example comprises: a medication instruction information acquisition unit 12 that acquires medication instruction information including medicine information indicating a packaged medicine and user information indicating a user who takes the medicine; a user checking unit 14 that checks whether or not a user corresponds to the user information in the medication instruction information acquired by the medication instruction information acquisition unit 12; a medicine package holding unit 16 that holds a medicine package in which the medicine is packaged; a medicine package providing unit 18 that takes out the medicine package corresponding to the user checked by the user checking unit 14 from the medicine package holding unit 16 and provides the medicine package to the user; a medicine package checking unit 20 that checks whether or not the medicine package (or the medicine in the medicine package) taken out from the medicine package holding unit 16 corresponds to the medicine information in the medication instruction information acquired by the medication instruction information acquisition unit 12; an action recognition unit 22 that recognizes an action of the user; a medication determination unit 24 that determines whether or not medication has been performed according to the medication instruction information acquired by the medication instruction information acquisition unit 12 based on the medication instruction information acquired by the medication instruction information acquisition unit 12, a checking result of the user checking unit 14, a checking result of the medicine package checking unit 20, and a recognition result of the action recognition unit 22; a recording unit 26 that records the medication instruction information and medication result information including the determination result of the medication determination unit 24, for each user, so as to be associated with each other; an output unit 28 that outputs the medication instruction information and the medication result information including the determination result of the medication determination unit 24, for each user, so as to be associated with each other; an overall controller 30 that performs overall control of each unit of the medication support robot 200A; and a storage unit 40 that stores a program and information necessary for executing the program.

There are various methods of medication instruction information acquisition by the medication instruction information acquisition unit 12.

First, there is a method of acquiring medication instruction information from the database 300 through a network. The medication instruction information acquisition unit 12 may acquire the medication instruction information from the packaging apparatus 120, the audit support apparatus 130, or the management apparatus 140 through a network. In this example, the medication instruction information acquisition unit 12 acquires information acquired at the time of reception by the reception apparatus 110, information acquired at the time of packaging by the packaging apparatus 120, and information acquired at the time of audit by the audit support apparatus 130 through a network, so that the acquired information can be reused as medication instruction information.

Second, there is a method of acquiring medication instruction information from the packaging material of the medicine package 52. For example, the medication instruction information acquisition unit 12 acquires at least a part of the medication instruction information by reading a code or a character attached to the packaging material of the medicine package 52.

The medicine information in the medication instruction information in this example includes identification information (medicine package identifier (ID)) of the medicine package 52, identification information (medicine identifier (ID)) of the medicine 2 in the medicine package 52, dosage information indicating the amount (for example, the number) of the medicine 2 in the medicine package 52, and medication time information indicating the time (medication time) to take the medicine 2. The medication time information in this example is associated with the user's meal time. The user information in the medication instruction information in this example includes the user's identification information (user identifier (ID)). The medication instruction information is not particularly limited to the medicine information and the user information.

There are various methods of user checking by the user checking unit 14.

First, there is a method of checking whether or not a user corresponds to the user information in the medication instruction information by performing image recognition on an image obtained by imaging the user (hereinafter, referred to as a "user image"). For example, the user checking unit 14 is configured to include a camera for imaging a user. For example, the user checking unit 14 checks whether or not a user in the vicinity of the medication support robot 200A corresponds to the user information in the medication instruction information by image recognition for which a master image of the user stored in the database 300 in advance is compared with a user image obtained by imaging the user. That is, the user checking unit 14 checks whether or not the user is a correct user.

Second, there is a method of checking whether or not a user corresponds to the user information in the medication instruction information by reading a code attached to the user's worn item (for example, a wristband worn on the wrist). For example, the user checking unit 14 is configured to include a code reader that reads a code attached to the user's worn item. For example, the user checking unit 14 checks whether or not a user in the vicinity of the medication support robot 200A corresponds to the user information in the medication instruction information by comparing a user ID included in the user information of the medication instruction information, which is a user ID stored in the database 300 in advance, with a user ID corresponding to the code read by the code reader. That is, the user checking unit 14 checks whether or not the user is a correct user.

The method of user checking by the user checking unit 14 is not limited to the methods described above. For example, user checking may be performed by voice recognition.

The medicine package holding unit 16 in this example holds the medicine package bandage 54 shown in FIG. 2, for example. The medicine package holding unit 16 may hold the medicine package bandage 54 shown in FIG. 4. In the medicine package bandage 54 shown in FIG. 4, a header portion 58 in which the medicine 2 is not packaged is provided. On the packaging material of the header portion 58, a user name 61, a medication time 62 (in this example, a medication start date, a correspondence relationship between meal time and medication time, and medication days), a user ID 63, and a medication instruction number 64 for identifying medication instruction information are printed by the packaging apparatus 120. In addition, on the packaging material of the header portion 58 in this example, a code 65 (in this example, a two-dimensional code) is printed by the packaging apparatus 120. In the code 65, for example, link information to medication instruction information for each user stored in the database 300 is encoded. In the code 65, only a user ID 63 may be encoded, or a medication instruction number 64 may be encoded, or link information to the user ID 63 or the medication instruction number 64 stored in the database 300 may be encoded.

Although the strip-shaped medicine package bandage 54 in which a plurality of medicine packages 52 are continuously provided has been described with reference to FIGS. 2 and 4. However, the package form of the medicine 2 is not particularly limited to such a case. For example, the medicine 2 may be packaged in a plastic medicine case, and the medicine package holding unit 16 may hold the medicine case.

In a case where the medicine package 52 is taken out from the medicine package holding unit 16, the medicine package providing unit 18 in this example cuts out one medicine package 52 from the medicine package bandage 54 and provides the one medicine package 52 to the user. In a case where the medicine 2 is packaged in a medicine case, one medicine case is taken out from the medicine package holding unit 16.

There are various methods of medicine package checking (or medicine checking) by the medicine package checking unit 20.

Figure 5:
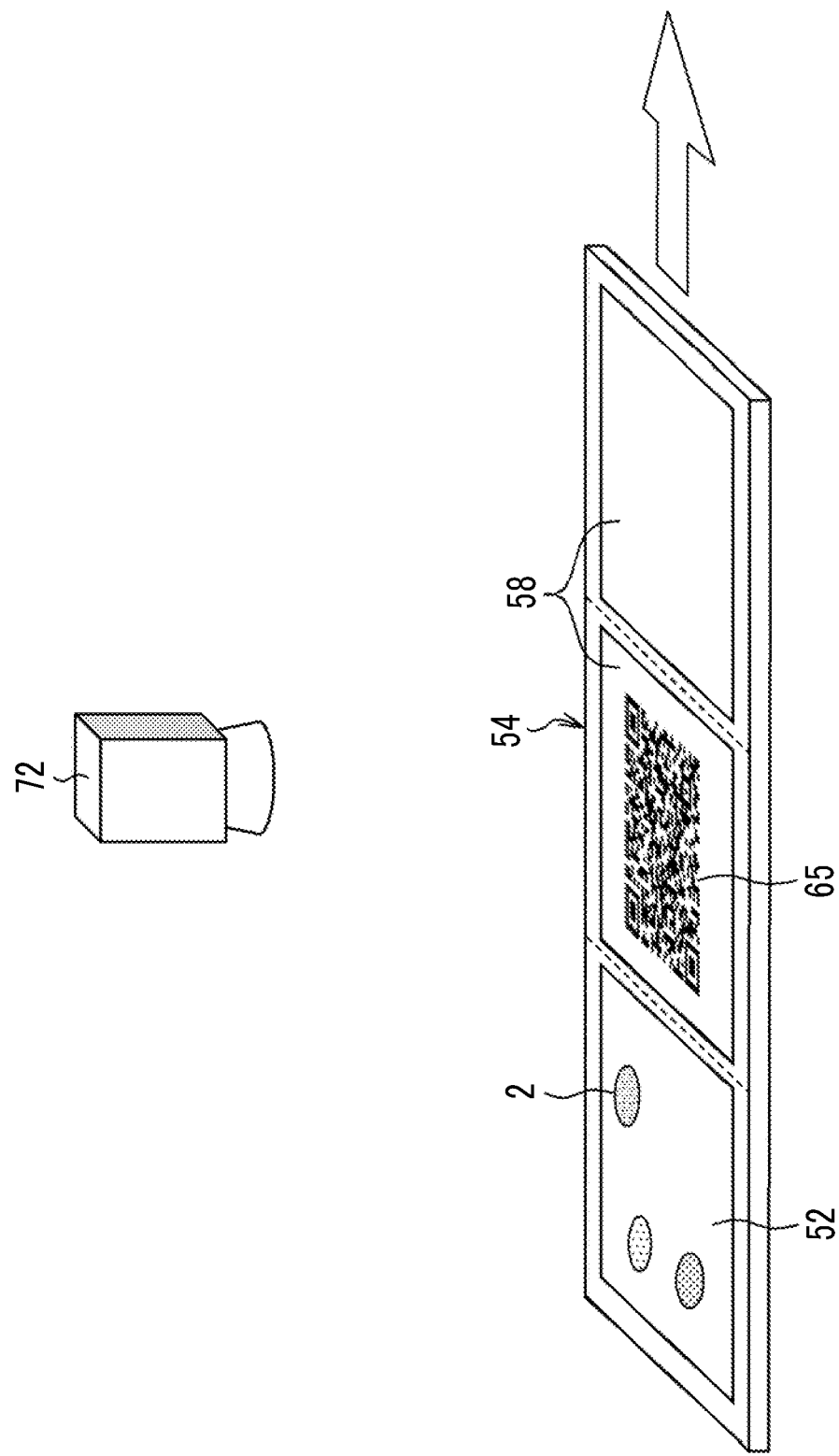
FIG. 5 is an explanatory diagram of code reading in the packaging example of FIG. 4.

First, as shown in FIG. 5, in the medication support robot 200A, the medicine package checking unit 20 checks whether or not the medicine package 52 taken out from the medicine package holding unit 16 (or the medicine package 52 currently held in the medicine package holding unit 16) is correct by reading the code 65 (in this example, a two-dimensional code) attached to the packaging material of the medicine package 52 using a code reader 72 and acquiring information corresponding to the read code 65 from the database 300. For example, in a case where the medication instruction information acquired in advance by the medication instruction information acquisition unit 12 includes a medicine package ID, it is checked whether or not the medicine package 52 is correct by comparing the medicine package ID acquired from the database 300 with the medicine package ID in the medication instruction information acquired in advance based on the code 65 of the packaging material. In a case where the medication instruction information acquired in advance by the medication instruction information acquisition unit 12 includes a medicine ID, it is checked whether or not the medicine 2 in the medicine package 52 is correct by comparing the medicine ID acquired from the database 300 with the medicine ID in the medication instruction information acquired in advance based on the code 65 of the packaging material. In this method, the medicine package checking unit 20 is configured to include the code reader 72. The code 65 can be attached to the packaging material by the packaging apparatus 120 or the audit support apparatus 130. The code attached to the packaging material is a two-dimensional code (for example, a QR code (registered trademark)) in this example, but the present invention is not limited thereto. A one-dimensional code (barcode), a radio frequency identifier (RFID), and the like may be applied. The medicine package checking unit 20 may check the medicine package 52 (or the medicine 2 in the medicine package 52) by optically reading a character attached to the packaging material and acquiring information corresponding to the character from the database 300.

Figure 6:
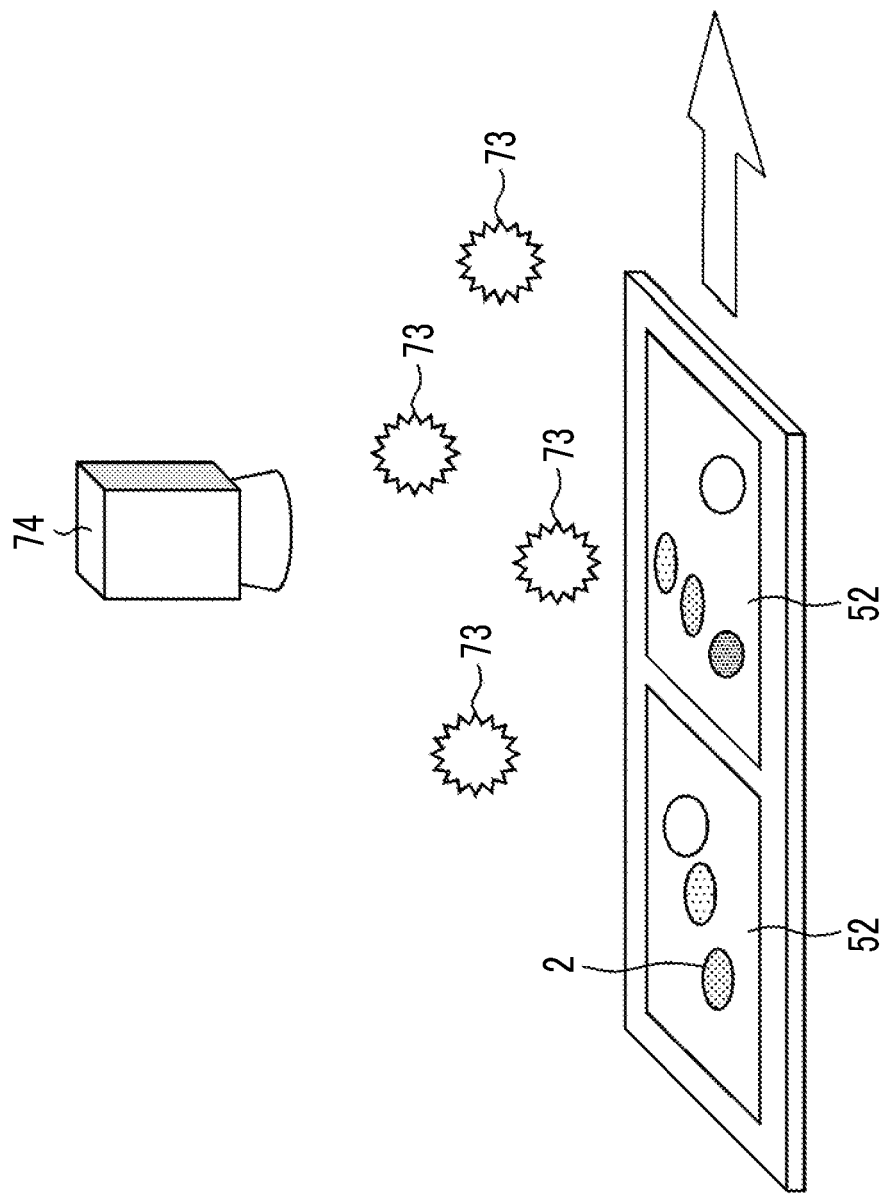
FIG. 6 is an explanatory diagram of an example of medicine package imaging.
Figure 7:
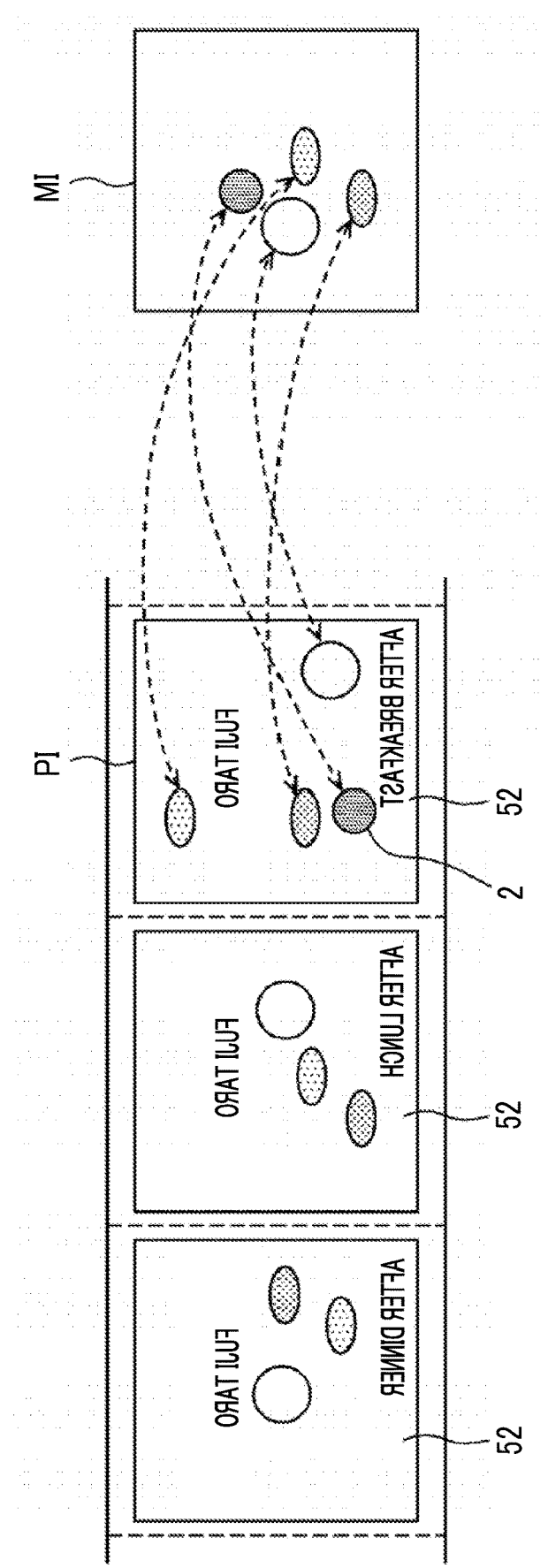
FIG. 7 is an explanatory diagram of an example of medicine image recognition.

Second, as shown in FIG. 6, in the medication support robot 200A, the medicine package checking unit 20 checks whether or not the medicine 2 in the medicine package 52 taken out from the medicine package holding unit 16 (or the medicine 2 in the medicine package 52 held in the medicine package holding unit 16) is correct by imaging the medicine package 52 using a camera 74 and performing image recognition on a medicine package image obtained by the imaging. In this method, the medicine package checking unit 20 is configured to include a light source 73 for illuminating the medicine package 52 from the periphery of the medicine package 52 and the camera 74 for imaging the illuminated medicine package 52, for example. For example, as shown in FIG. 7, each medicine 2 in the medicine package 52 is recognized by image recognition for which a master image MI stored in the database 300 is compared with a medicine package image PI, which is obtained by imaging the medicine package 52 with the camera 74, for each medicine 2, and it is checked whether or not each medicine 2 in the medicine package 52 corresponds to the medicine information in the medication instruction information. The master image MI can be captured by the packaging apparatus 120 or the audit support apparatus 130 and stored in the database 300. In the example shown in FIG. 7, a case is shown in which the medicine package 52 having one surface, on which the user name and the medication time are printed, is imaged from the other surface (the user name and the medication time are mirrored). However, printing of the user name and the medication time is not essential, and the imaging direction may be appropriately selected.

Figure 8:
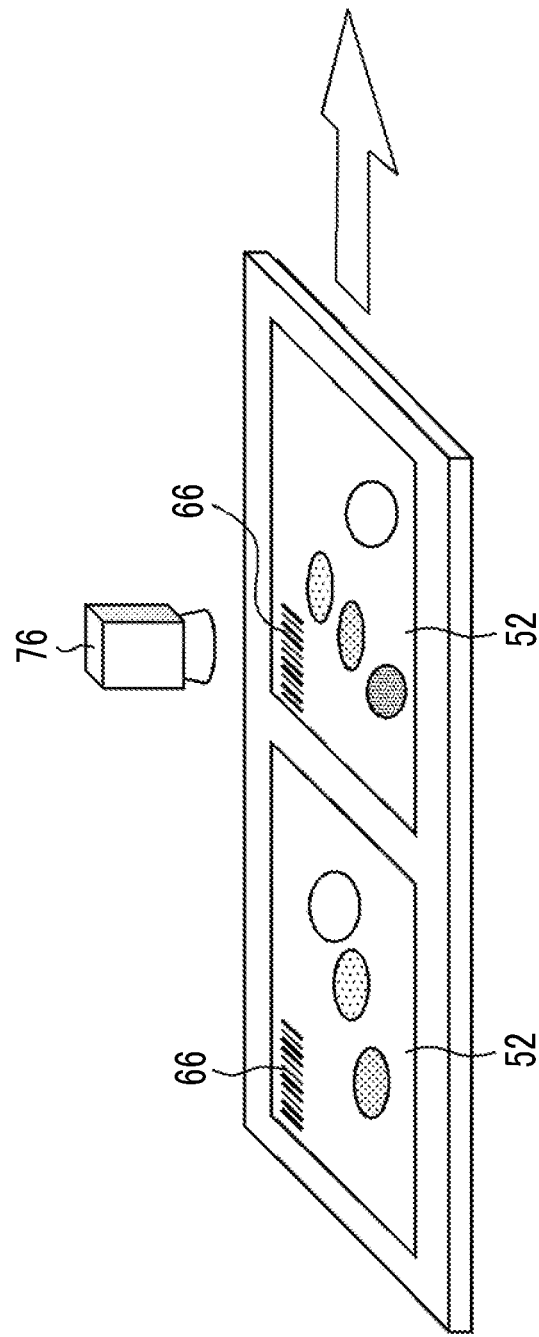
FIG. 8 is an explanatory diagram of an example of code reading for each medicine package.
Figure 9:
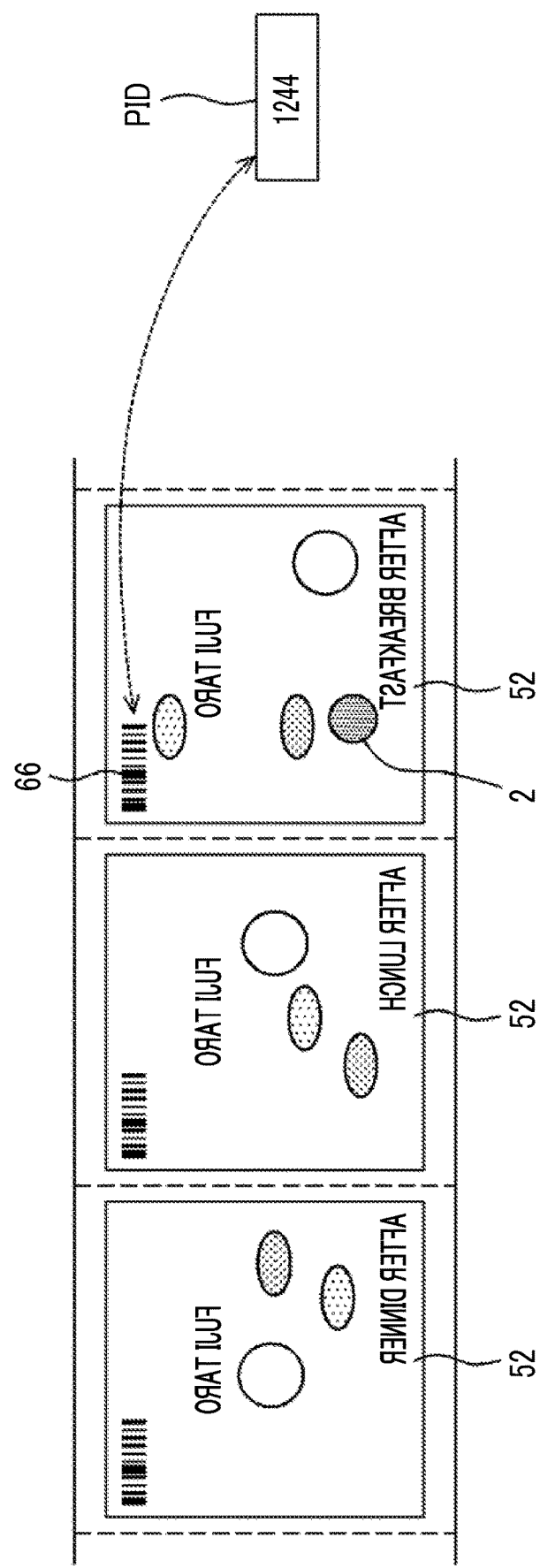
FIG. 9 is an explanatory diagram of an example of code matching.

Third, as shown in FIG. 8, in the medication support robot 200A, the medicine package checking unit 20 checks whether or not the medicine package 52 taken out from the medicine package holding unit 16 (or the medicine package 52 currently held in the medicine package holding unit 16) is correct by reading a code 66 (in this example, a one-dimensional code) attached to the packaging material for each medicine package 52 using a code reader 76 and acquiring information corresponding to the read code 66 from the database 300. For example, as shown in FIG. 9, the medicine package checking unit 20 can check whether or not the medicine package 52 is correct by comparing the medicine package ID obtained by decoding the code 66 with the medicine package ID indicated by the medication instruction information, which is a medicine package ID (PID) stored at the time of packaging or audit in the database 300. In this method, the medicine package checking unit 20 is configured to include the code reader 76. For example, as shown in FIG. 10, in the database 300, the medicine package ID (PID) and the medication time are stored so as to be associated with each other for each user. The code attached to the packaging material is a one-dimensional code (so-called barcode) in this example, but the present invention is not limited thereto. The code may be a two-dimensional code. Instead of the code, a radio frequency identifier (RFID) and the like may be applied.

The checking of the medicine package or the checking of the medicine in the medicine package by the medicine package checking unit 20 can also be performed before the medicine package is held by the medicine package holding unit 16 (for example, at the time of loading).

The action recognition unit 22 in this example recognizes the user's eating action and medication action. As described above, the medication instruction information in this example includes medication time information indicating the time to take a medicine, and the action recognition unit 22 in this example recognizes at least the medication time of the user.

The medication time indicates, for example, one of "morning", "daytime", and "night" and one of "before meal" and "after meal". For example, in a case where the instruction is "before breakfast", the medicine is taken about 30 minutes before breakfast. For example, in a case where the instruction is "after breakfast", the medicine is taken about 30 minutes after breakfast. For example, in a case where the instruction is "between meals", the medicine is taken about two hours after a meal. An instruction may be given as a specific time, such as "five minutes before a meal".

There are various methods of user action recognition by the action recognition unit 22.

First, there is a method in which the action recognition unit 22 recognizes the user action by performing image recognition on a user image obtained by imaging the user with a camera. For example, the action recognition unit 22 recognizes a face portion in the user image, and performs image recognition regarding whether or not food or medicine has entered the user's mouth. Artificial intelligence may be used for image recognition.

Second, there is a method in which the action recognition unit 22 recognizes the user's action through interaction with the user. The interaction is not limited to voice communication. For example, communication based on a character or a sign language may be applied.

The medication determination unit 24 in this example determines whether or not medication has been performed according to the medication time information based on the medication time information and the recognition result of the eating action and the medication action.

The recording unit 26 is configured by, for example, a communication device, and performs recording on the database 300. The recording unit 26 may be configured by a recording medium interface device capable of performing writing into a predetermined recording medium, such as a memory card. The recording unit 26 records the determination result of the medication determination unit 24, which indicates whether or not the user corresponding to the user information in the medication instruction information has actually taken the medicine in the medicine package corresponding to the medicine information in the medication instruction information (or the medicine corresponding to the medicine information in the medication instruction information). In addition, it is preferable that the recording unit 26 records whether or not the correspondence relationship between the eating action and the medication action recognized by the action recognition unit 22 is the same as the medication time information in the medication instruction information.

The output unit 28 is configured by, for example, a communication device, and outputs information to the management apparatus 140. The output unit 28 may be configured to include a display device or a printing device. The output of the medication result information by the output unit 28 is not limited to the transmission output using a communication device. Display output using a display device and print output using a print device may be applied. The output unit 28 outputs the determination result of the medication determination unit 24, which indicates whether or not the user corresponding to the user information in the medication instruction information has actually taken the medicine in the medicine package corresponding to the medicine information in the medication instruction information (or the medicine corresponding to the medicine information in the medication instruction information). In addition, it is preferable to output whether or not the correspondence relationship between the eating action and the medication action recognized by the action recognition unit 22 is the same as the medication time information in the medication instruction information.

The overall controller 30 is configured by, for example, a central processing unit (CPU).

The storage unit 40 is configured by a temporary storage device and a non-temporary storage device. The temporary storage device is, for example, a random access memory (RAM). The non-temporary storage device is, for example, a read only memory (ROM) or an electrically erasable programmable read only memory (EEPROM). The non-temporary storage device stores a program.

Figure 4:
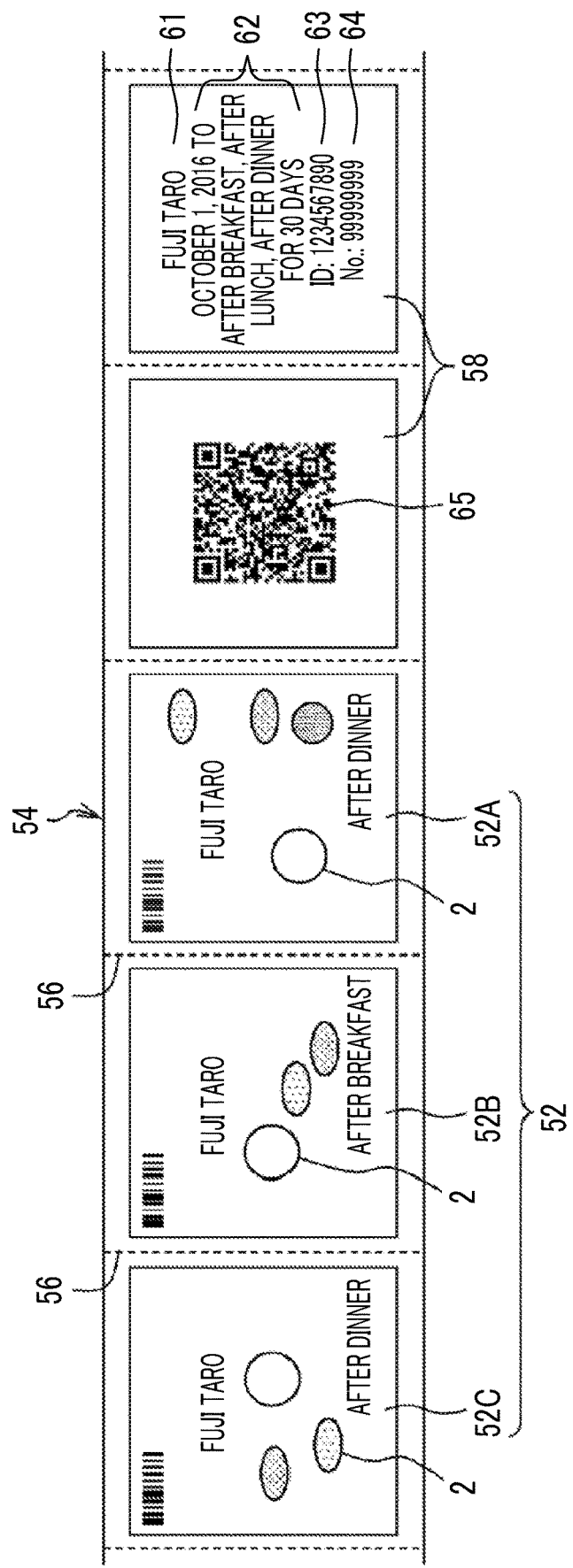
FIG. 4 is an explanatory diagram of a packaging example in which medicine packages having a header portion are provided.
Figure 11:
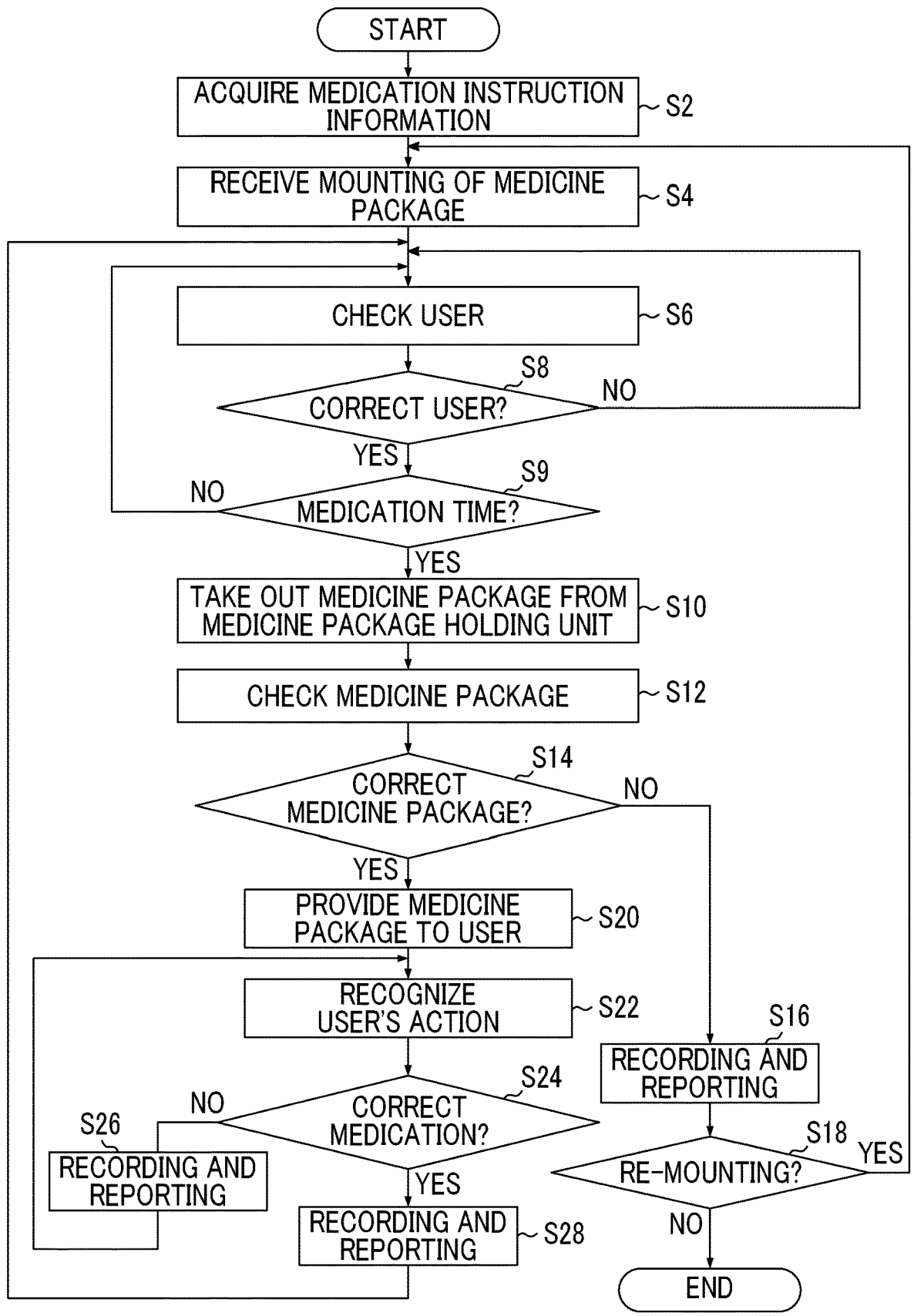
FIG. 11 is a flowchart showing the flow of an example of a medication support process.

FIG. 11 is a flowchart showing the flow of an example of the medication support process in the medication support robot 200A shown in FIG. 4. The medication support process in this example is executed according to a program under the control of the CPU configuring the overall controller 30.

First, the medication instruction information acquisition unit 12 acquires medication instruction information including medicine information and user information from the database 300 (step S2). The medication instruction information may be acquired directly from at least one of the packaging apparatus 120 or the audit support apparatus 130.

The medicine package holding unit 16 receives the mounting of the medicine package 52 in which the medicine 2 is packaged for each one medication (step S4). That is, the medicine package 52 in which the medicine 2 is packaged is held by the medicine package holding unit 16. For example, the medicine package bandage 54 shown in FIG. 2 or 4 is mounted on the medicine package holding unit 16.

In a state in which the medicine packages 52 for a plurality of medications are held by the medicine package holding unit 16, the user checking unit 14 checks whether or not the user present in the vicinity of the medication support robot 200A is a user corresponding to the user information in the medication instruction information (step S6). This step is one form of "user checking step". The medication determination unit 24 determines whether or not the user present in the vicinity of the medication support robot 200A is a correct user according to the user information in the medication instruction information based on the checking result of the user checking unit 14 (step S8).

In a case where it is determined that the user present in the vicinity of the medication support robot 200A is not a correct user (in the case of NO in step S8), the process returns to step S6. That is, in a case where there is another person in the vicinity of the medication support robot 200A, the user is checked.

In a case where it is determined that the user present in the vicinity of the medication support robot 200A is a correct user (in the case of YES in step S8), the medication determination unit 24 determines whether or not this is the medication time (step S9).

In a case where it is determined that this is not the medication time (in the case of NO in step S9), the process returns to step S6.

In a case where it is determined that this is the medication time (in the case of YES in step S9), the medicine package providing unit 18 takes out the medicine package 52 corresponding to the checked correct user from the medicine package holding unit 16 (step S10), and the medicine package checking unit 20 checks whether or not the medicine package 52 taken out from the medicine package holding unit 16 (or the medicine 2 in the medicine package 52 that has been taken out) corresponds to the medicine information in the medication instruction information (step S12). This step is one form of "medicine package checking step". The medication determination unit 24 determines whether or not the medicine package 52 taken out from the medicine package holding unit 16 (or the medicine 2 in the medicine package 52 that has been taken out) is a correct medicine package (or a correct medicine) according to the medication instruction information based on the checking result of the medicine package checking unit 20 (step S14).

In a case where it is determined that the medicine package 52 taken out from the medicine package holding unit 16 (or the medicine 2 in the medicine package 52 that has been taken out) is not a correct medicine package (or a correct medicine) (in the case of NO in step S14), the fact that the correct medicine package has not been taken out is recorded and reported (step S16), and it is determined whether or not re-mounting of a new medicine package on the medicine package holding unit 16 is to be performed (step S18). In a case where it is determined that re-mounting of a medicine package is to be performed (in the case of YES in step S18), the process returns to step S4. In a case where it is determined that re-mounting of a medicine package is not to be performed (in the case of NO in step S18), this process is ended.

In a case where it is determined that the medicine package 52 taken out from the medicine package holding unit 16 (or the medicine 2 in the medicine package 52 that has been taken out) is a correct medicine package (or a correct medicine) (in the case of YES in step S14), the medicine package providing unit 18 provides the user with the medicine package taken out from the medicine package holding unit 16 (step S20), and the action recognition unit 22 recognizes the user's action (step S22). The action recognition unit 22 in this example recognizes the user's medication action. This step is one form of "action checking step".

The medication determination unit 24 determines whether or not the medication action has been performed according to the medication instruction information (step S24). That is, it is determined whether or not correct medication has been performed.

In a case where it is determined that the correct medication action has not been performed (in the case NO in step S24), recording and reporting are performed to indicate that the correct medication has not been performed (step S26).

In a case where it is determined that the correct medication has been performed (in the case YES in step S24), the fact that the correct medication has been performed is recorded and reported (step S28).

In the above-described example of the medication support process, the case of recognizing the medication action as the recognition of the user action is shown. However, both the eating action and the medication action may be recognized, and whether or not the correspondence relationship between the eating action and the medication action is the same as the medication time information in the medication instruction information may be checked.

According to this example, the medication instruction information including the medicine information indicating the packaged medicine and the user information indicating the user who takes the medicine is acquired, and it is checked whether or not the user corresponds to the user information in the medication instruction information. The medicine package corresponding to the checked user is taken out, and it is checked whether or not the medicine package or the medicine in the medicine package corresponds to the medicine information in the medication instruction information. The user's action is recognized, and it is determined whether or not medication has been performed according to the medication instruction information based on the medication instruction information, the user checking result, the checking result of the medicine package or the medicine, and the user action recognition result. In this manner, it is reliably checked that the correct user has taken the correct medicine. In addition, according to this example, it is possible to determine an appropriate medication timing by acquiring the medication time information and recognizing the user's eating action. Therefore, it is possible to reliably check that the user has taken the medicine at an appropriate time, such as before a meal or after a meal. For example, even in a case where the user is a too old person or has dementia, it is possible to reliably check that the correct user has taken the correct medicine.

Figure 12:
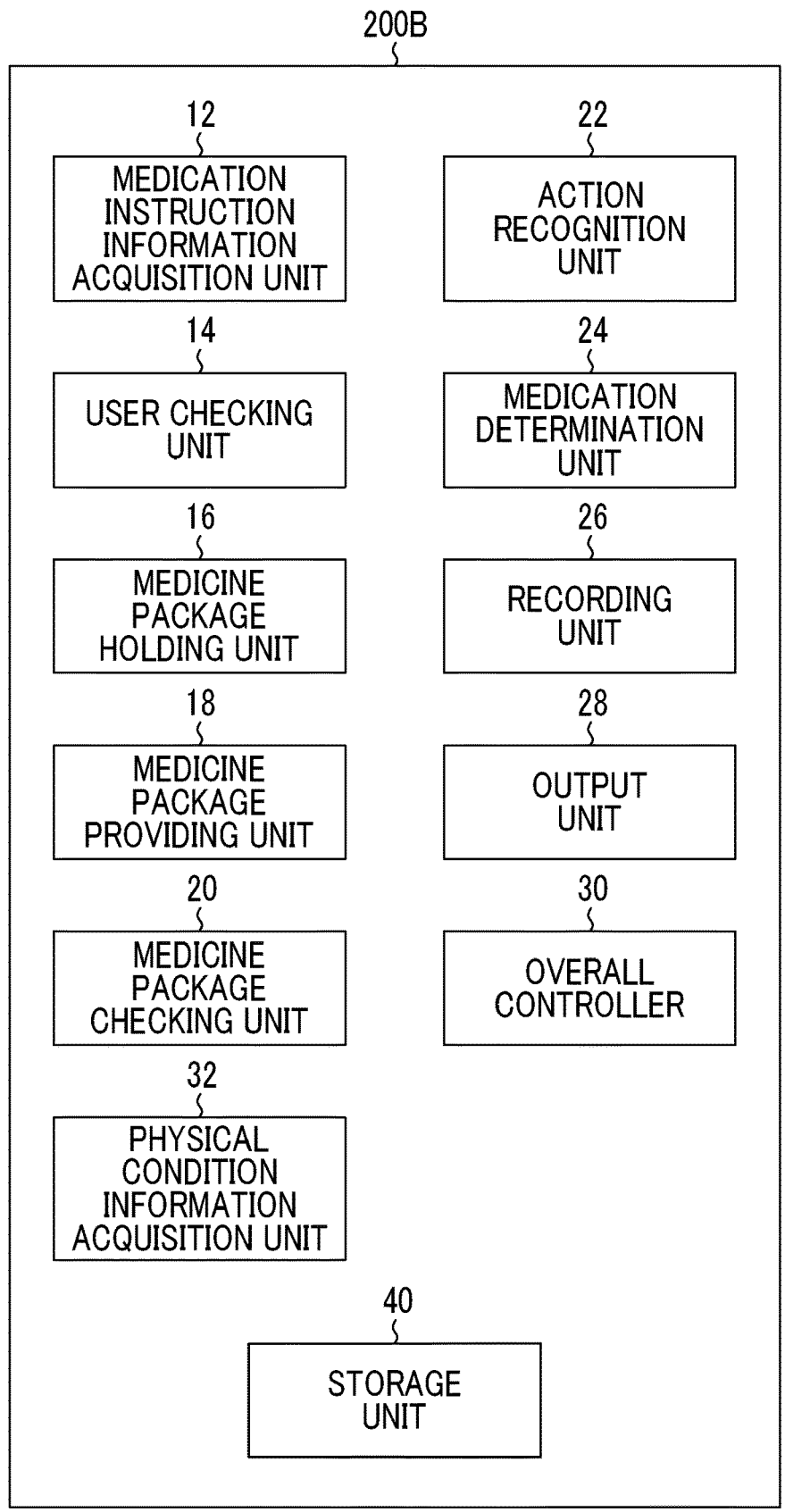
FIG. 12 is a block diagram showing an example of the internal configuration of a medication support robot in a second embodiment.

FIG. 12 is a block diagram showing a configuration example of a medication support robot in a second embodiment. The same components as those of the medication support robot 200A in the first embodiment shown in FIG. 3 are denoted by the same reference numerals, and the content described above will be omitted below.

A medication support robot 200B of the present embodiment comprises a physical condition information acquisition unit 32 that acquires physical condition information indicating the physical condition of the user. The physical condition information acquisition unit 32 includes, for example, a body temperature sensor for detecting the body temperature of the user, a pulse sensor for detecting the pulse of the user, a blood pressure sensor for detecting the blood pressure of the user, a blood sugar level sensor for detecting the blood sugar level of the user, a scale for measuring the weight of the user, and a pedometer for measuring the number of steps taken by the user. The physical condition information acquisition unit 32 may include an environment sensor (for example, a thermometer for measuring the temperature and a hygrometer for measuring the humidity) for detecting a living environment that affects the physical condition of the user. The user may be imaged by a camera, and information regarding the user's physical condition may be acquired from the user image.

The physical condition information acquisition unit 32 in this example is configured by a sensor provided in the medication support robot 200B. However, the physical condition information of the user may be acquired from an external device of the medication support robot 200B by communication or the like.

The output unit 28 in this example outputs the physical condition information acquired by the physical condition information acquisition unit 32 to the database 300 or the management apparatus 140. That is, an administrator (for example, a pharmacist) of the management apparatus 140 can grasp a physical condition change (vital sign) of the user in real time. In a case where the output unit 28 outputs living environment information, it is possible to grasp the living environment of the user in real time together with the physical condition of the user using the management apparatus 140. The management apparatus 140 may be disposed at a place other than the prescription pharmacy. In this case, a person (for example, a doctor, a nurse, and a carer) other than the pharmacist can grasp the physical condition and the living environment of the user in real time using the management apparatus 140.

Figure 13:
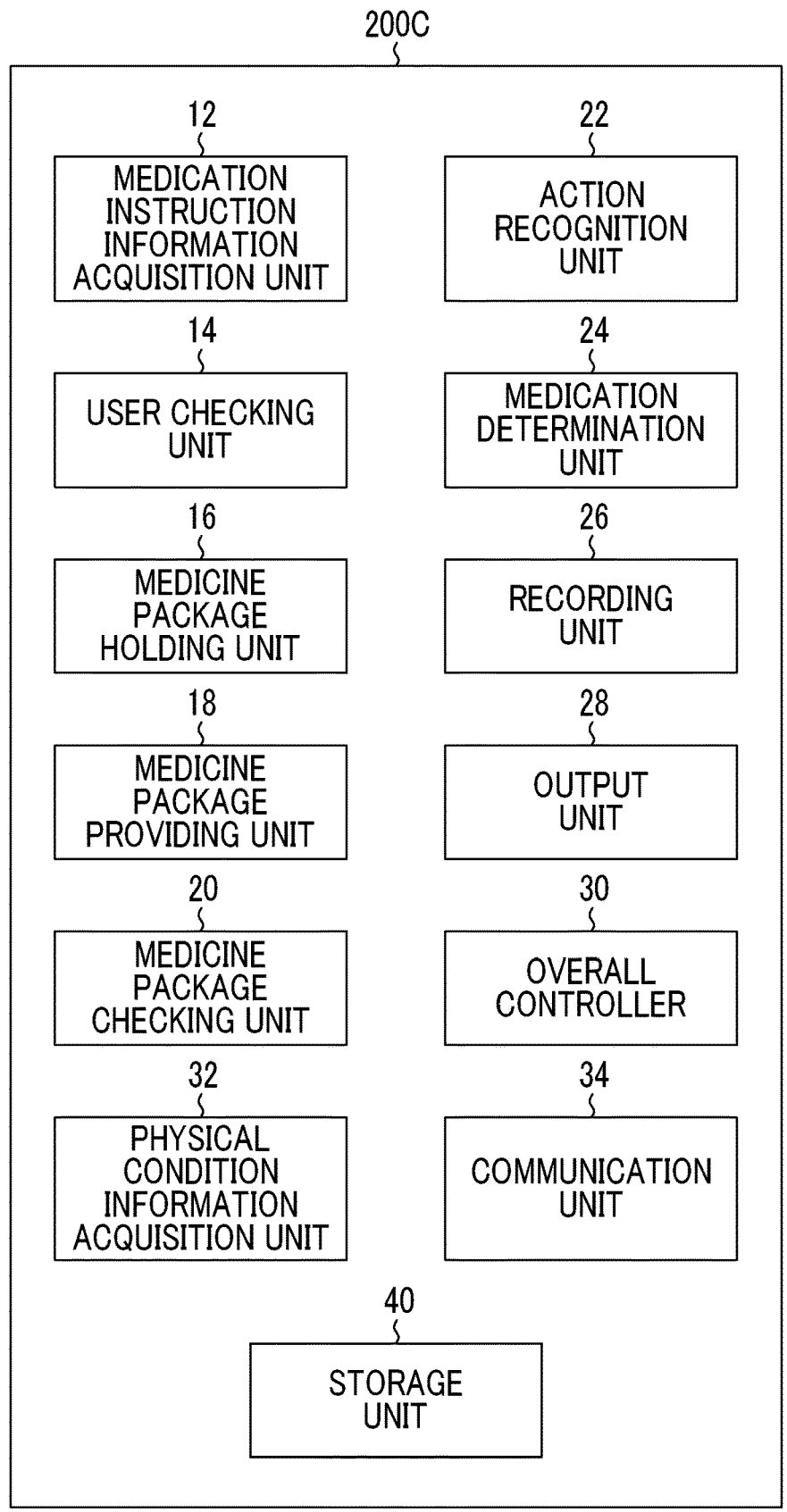
FIG. 13 is a block diagram showing an example of the internal configuration of a medication support robot in a third embodiment.

FIG. 13 is a block diagram showing a configuration example of a medication support robot in a third embodiment. The same components as those of the medication support robot 200A in the first embodiment shown in FIG. 3 and the medication support robot 200B in the second embodiment shown in FIG. 12 are denoted by the same reference numerals, and the content described above will be omitted below.

A medication support robot 200C of the present embodiment comprises a communication unit 34 that makes an inquiry to the user. The inquiry to the user is not limited to voice communication. For example, communication based on a character or a sign language may be applied.

The communication unit 34 in this example performs two-way communication with the management apparatus 140 to receive the inquiry content from the administrator (for example, a pharmacist) of the management apparatus 140 and transmit the user's answer acquired by the communication unit 34 to the management apparatus 140. That is, the administrator of the management apparatus 140 can interact with the user through the medication support robot 200C. The management apparatus 140 may be disposed at a place other than the prescription pharmacy. In this case, a person (for example, a doctor, a nurse, and a carer) other than the pharmacist can make an inquiry (for example, ask a question) to the user through the management apparatus 140 and the medication support robot 200C. For example, by the inquiry to the user, the administrator of the management apparatus 140 can grasp a medicine that the user cannot easily take and select a generic medicine that the user can easily take.

<Variations>As a form of using the medication support apparatus according to the present invention, one medication support apparatus may perform medication support for one user, or may perform medication support for a plurality of users.

Figure 14:
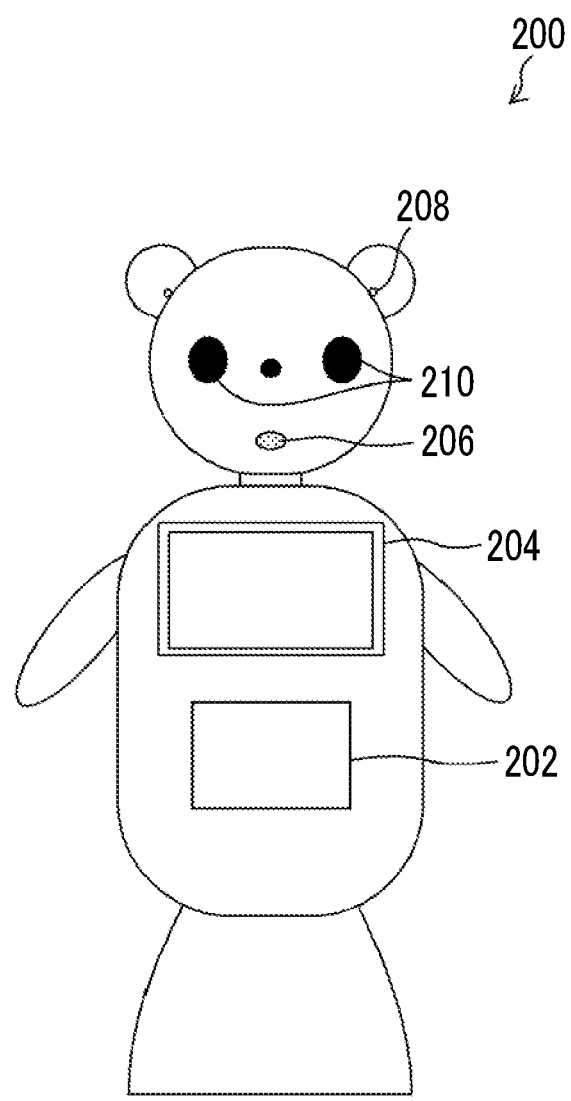
FIG. 14 is an external diagram of an example of a medication support robot, in which one medicine package discharge port is provided.

FIG. 14 is an external diagram of an example of a medication support robot in which one discharge port of the medicine package 52 is provided. The medication support robot 200 in this example includes one discharge port 202 for providing a medicine package to one user. The medication support robot 200 comprises a display device 204, a speaker 206, a microphone 208, and a camera 210 that are used for interaction with the user and the like. The medication support robot 200 may be configured to be self-propelled or non-self-propelled. In a case where the medication support robot 200 can be self-propelled, the medication support robot 200 can be used not for a single user but for a plurality of users.

Figure 15:
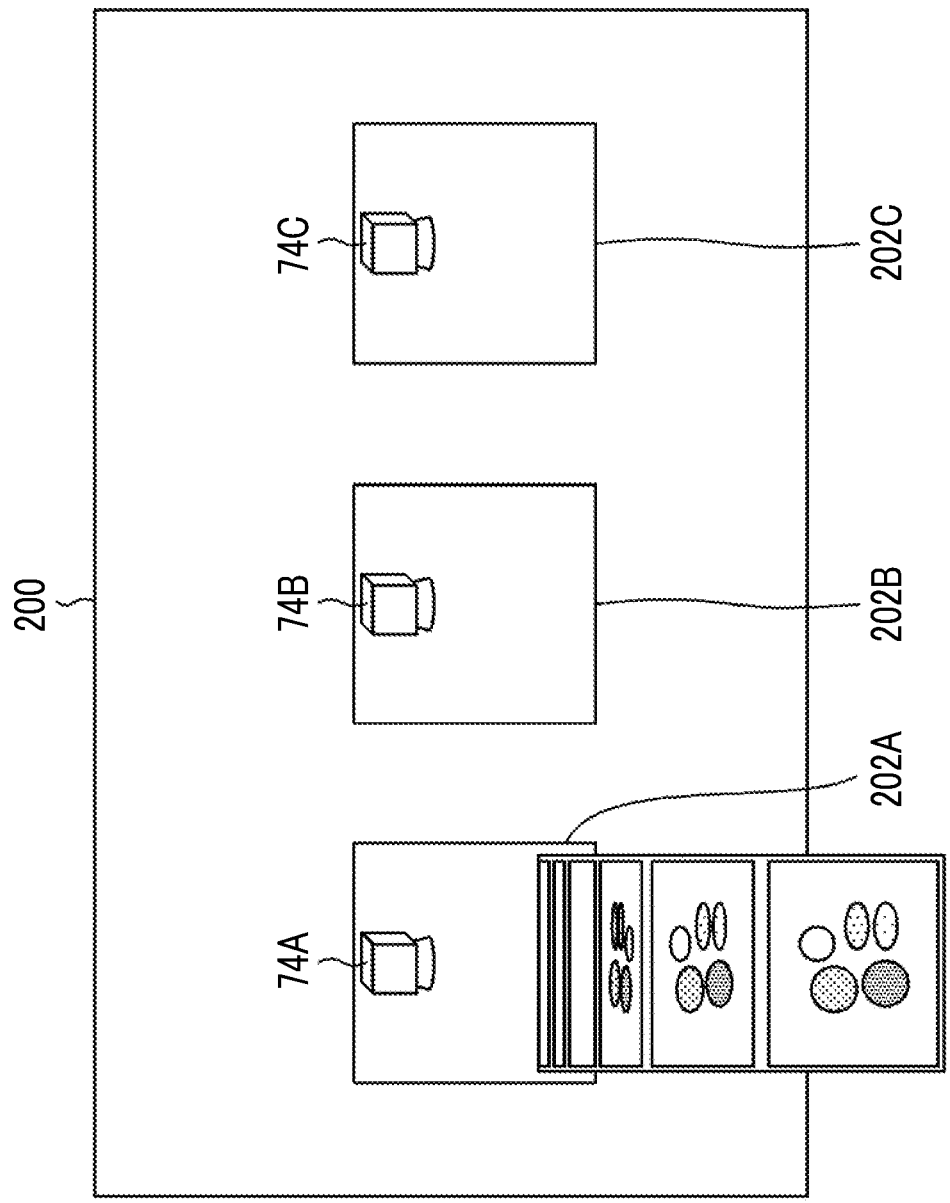
FIG. 15 is an external diagram of an example of a medication support robot in which a plurality of medicine package discharge ports are provided.

FIG. 15 is an external diagram of an example of a medication support robot in which a plurality of medicine package discharge ports are provided. The medication support robot in this example may include a plurality of discharge ports 202A, 202B, and 202C for providing a medicine package to each of a plurality of users. In addition, cameras 74A, 74B, and 74C for imaging the medicine package are provided in the plurality of discharge ports 202A, 202B, and 202C, respectively. For example, the first discharge port 202A can be used for "person A", the second discharge port 202B can be used for "person B", and the third discharge port 202C can be used for "person C".

In a case where the medication support robot 200A shown in FIG. 15 is used for a single user, the first discharge port 202A may be used for "morning", the second discharge port 202B may be used for "daytime", and the third discharge port 202C may be used for "evening".

The medication instruction information acquisition unit 12, the user checking unit 14, the medicine package holding unit 16, the medicine package providing unit 18, the medicine package checking unit 20, the action recognition unit 22, the medication determination unit 24, the overall controller 30, the physical condition information acquisition unit 32, and the communication unit 34 shown in FIGS. 3, 12, and 13 described above can be configured to includes various processors shown below. The various processors include a central processing unit (CPU) that is a general-purpose processor that executes various kinds of processing with software (program), a programmable logic device (PLD) that is a processor whose circuit configuration can be changed after manufacture, such as a field programmable gate array (FPGA), and a dedicated electric circuit that is a processor having a circuit configuration that is designed for exclusive use in order to execute specific processing, such as an application specific integrated circuit (ASIC). In the embodiment described above, the function of the medication support robot 200A (200A, 200B, and 200C) may be realized by one of the various processors, or may be realized by two or more processors of the same type or different types (for example, a plurality of FPGAs or a combination of a CPU and an FPGA). Alternatively, a plurality of functions may be realized by one processor. As an example of realizing a plurality of functions with one processor, as represented by a system on chip (SoC) or the like, there is a form of using a processor that realizes the function of the entire system having a plurality of functions with one integrated circuit (IC) chip. Thus, various functions are realized by using one or more of the above-described various processors as a hardware structure. In addition, the hardware structure of these various processors is an electrical circuit (circuitry) in the form of a combination of circuit elements, such as semiconductor elements.

While the forms for implementing the present invention have been described, the present invention is not limited to the embodiments and the modification examples described above, and various modifications can be made without departing from the scope of the present invention.

EXPLANATION OF REFERENCES

1: prescription information
2: medicine
3: user
12: medication instruction information acquisition unit
14: user checking unit
16: medicine package holding unit
18: medicine package providing unit
20: medicine package checking unit
22: action recognition unit
24: medication determination unit
26: recording unit
28: output unit
30: overall controller
32: physical condition information acquisition unit
34: communication unit
40: storage unit
52 (52A, 52B, 52C): medicine package
54: medicine package bandage
56: perforation
58: header portion
61: user name
62: medication time
63: user ID
64: medication instruction number
65, 66: code
72: code reader
73: light source
74 (74A, 74B, 74C): camera
76: code reader
110: reception apparatus
120: packaging apparatus
130: audit support apparatus
140: management apparatus
200 (200A, 200B, 200C): medication support robot (medication support apparatus)
202 (202A, 202B, 202C): discharge port
204: display device
206: speaker
208: microphone
210: camera
300: database
MI: master image
PI: medicine package image

What is claimed is:

1. A medication support apparatus, comprising:
a medication instruction information acquisition unit that acquires medication instruction information including medicine information indicating a packaged medicine, user information indicating a user who takes the medicine, and medication time information indicating a time to take the medicine associated with a meal time of the user;
a medicine package holding unit that holds a medicine package in which the medicine is packaged;
a user checking unit that checks whether or not a user corresponds to the user information;

a medicine package providing unit that takes out the medicine package corresponding to the checked user from the medicine package holding unit;

a medicine package checking unit that checks whether or not the medicine package or the medicine in the medicine package corresponds to the medicine information;

an action recognition unit that recognizes actions of taking the medicine and eating of the user through images obtained by imaging the user or interaction with the user; and a medication determination unit that determines whether or not the user has taken the medicine in compliance with the medication time information, according to the medication instruction information, a checking result of the user checking unit, a checking result of the medicine package checking unit, and a recognition result of the action recognition unit.

2. The medication support apparatus according to claim 1, further comprising:

a recording unit that records the medication instruction information and medication result information including a determination result of the medication determination unit, for each user, so as to be associated with each other.

3. The medication support apparatus according to claim 1, further comprising:

an output unit that outputs the medication instruction information and medication result information including a determination result of the medication determination unit, for each user, so as to be associated with each other.

4. The medication support apparatus according to claim 3, further comprising:

a physical condition information acquisition unit that acquires physical condition information indicating a physical condition of the user, wherein the output unit outputs the physical condition information acquired by the physical condition information acquisition unit.

5. The medication support apparatus according to claim 1, wherein the medication instruction information acquisition unit acquires at least a part of the medication instruction information by reading a code or a character attached to the medicine package.

6. The medication support apparatus according to claim 1, wherein the medicine package checking unit recognizes the medicine package or the medicine in the medicine package by reading a code or a character attached to the medicine package.

7. The medication support apparatus according to claim 1, wherein the medicine package checking unit recognizes the medicine package or the medicine in the medicine package by performing image recognition on an image obtained by imaging the medicine package.

8. The medication support apparatus according to claim 1, further comprising:

a communication unit that makes an inquiry to the user.

9. A medication support system, comprising:

the medication support apparatus according to claim 1; and at least one of a packaging apparatus for packaging the medicine or an audit support apparatus for supporting an audit of the medicine.

10. The medication support system according to claim 9, wherein the medication instruction information acquisition unit acquires the medication instruction information from at least one of the packaging apparatus or the audit support apparatus.

11. A medication support method, comprising:

a step of acquiring medication instruction information including medicine information indicating a packaged medicine, user information indicating a user who takes the medicine, and medication time information indicating a time to take the medicine associated with a meal time of the user;

a user checking step of checking whether or not a user corresponds to the user information;

a step of taking out a medicine package corresponding to the checked user from a medicine package holding unit that holds the medicine package in which the medicine is packaged;

a medicine package checking step of checking whether or not the medicine package or the medicine in the medicine package corresponds to the medicine information;

an action recognition step of recognizing actions of taking the medicine and eating of the user through images obtained by imaging the user or interaction with the user; and a step of determining whether or not the user has taken the medicine in compliance with the medication time information, according to the medication instruction information, a checking result of the user checking step, a checking result of the medicine package checking step, and a recognition result of the action recognition step.

12. A non-transitory, tangible computer-readable recording medium which records a program causing a computer to execute:

a step of acquiring medication instruction information including medicine information indicating a packaged medicine, user information indicating a user who takes the medicine, and medication time information indicating a time to take the medicine associated with a meal time of the user;

a user checking step of checking whether or not a user corresponds to the user information;

a step of taking out a medicine package corresponding to the checked user from a medicine package holding unit that holds the medicine package in which the medicine is packaged;

a medicine package checking step of checking whether or not the medicine package or the medicine in the medicine package corresponds to the medicine information;

an action recognition step of recognizing actions of taking the medicine and eating of the user through images obtained by imaging the user or interaction with the user; and a step of determining whether or not the user has taken the medicine in compliance with the medication time information, according to the medication instruction information, a checking result of the user checking step, a checking result of the medicine package checking step, and a recognition result of the action recognition step.

* * * * *